US00PP12225P2

(12) United States Plant Patent
Utecht

(10) Patent No.: US PP12,225 P2
(45) Date of Patent: Nov. 27, 2001

(54) GERANIUM PLANT NAMED 'FISLAMDA'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/323,109

(22) Filed: Jun. 1, 1999

(51) Int. Cl.[7] ..... A01H 5/00
(52) U.S. Cl. ..... Plt./332
(58) Field of Search ..... Plt./332, 324

(56) References Cited

U.S. PATENT DOCUMENTS

P.P. 10,350 * 4/1998 Utecht ..... Plt./87.12
P.P. 10,635 * 10/1998 Schumann et al. ..... Plt./87.12

FOREIGN PATENT DOCUMENTS 98-1356 4/1998 (CA) .
98-26-1420 4/1998 (CH) .
PEL 1357 9/1996 (DE) .
97/0955 9/1997 (EP) .
10922 5/1998 (JP) .
O 466 12/1998 (PL) .

OTHER PUBLICATIONS

Fischer catalogue 1998 (1998).
UPOV–ROM GTIM Computer Database 1999/02, GTI Jouve Retrieval Software, citations for 'Fislamda', 1997–1998.*

* cited by examiner

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of geranium plant named 'Fislamda', as described and illustrated, and particularly characterized by the combined features of purple-pink double flowers, large inflorescence, medium green, glossy foliage with distinct zonation, moderately vigorous growth, and early to medium flowering response.

1 Drawing Sheet

BACKGROUND OF THE INVENTION

The present invention comprises a new and distinct cultivar of geranium plant, botanically known as *Pelargonium peltatum,* and hereinafter referred to by the cultivar name 'Fislamda'.

'Fislamda' is a product of a planned breeding program which had the objective of creating new geranium cultivars with stable pink to purple-pink flower color and medium tall, well-branched plant habit.

'Fislamda' was originated from a hybridization made by the inventor, Angelika Utecht, in a controlled breeding program in Galdar, Gran Canaria, Spain, in 1994. The female parent was an unnamed seedling from the commercial variety 'M. J. Cole', which was characterized by intense purple-pink flower color, semi-double flower form, foliage with weak zonation, and relatively weak growth. The male parent of 'Fislamda' was 'Pilatus', an unpatented commercial variety having light-violet double flowers with distinct markings, distinctly zoned foliage, late flowering response, and weak growth.

'Fislamda' was selected as one flowering plant within the progeny of the stated cross by the inventor, Angelika Utecht, in 1995 in a controlled environment in Galdar, Gran Canaria, Spain.

The first act of asexual reproduction of 'Fislamda' was accomplished when vegetative cuttings were taken from the initial selection in autumn 1995 in a controlled environment in Galdar, Gran Canaria, Spain by Angelika Utecht. Horticultural examination of plants grown from these cuttings initiated in May 1996 in Hillscheid, Federal Republic of Germany, and continuing thereafter, has demonstrated that the combination of characteristics as herein disclosed for 'Fislamda' are firmly fixed and are retained through successive generations of asexual reproduction.

BRIEF DESCRIPTION OF THE INVENTION

The following traits have been repeatedly observed and are determined to be basic characteristics of 'Fislamda', which in combination distinguish this geranium as a new and distinct cultivar:

1. Intense purple-pink flower color;

2. Large double flowers arranged in relatively big, semi-spherically shaped inflorescence;

3. Medium-green foliage with distinct zonation;

4. Medium to tall, fairly round plant habit;

5. Early to medium flowering response; and

6. Large number of flowers and big buds that are developed at the beginning of flowering.

'Fislamda' has not been observed under all possible environmental conditions. The phenotype of the new cultivar may vary significantly with variations in environment such as temperature, light intensity and daylength without any change of genotype of the plant. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fislamda' are the patented varieties 'Flofetti' (U.S. Plant Pat. No. 10,635) and 'Fischic' (U.S. Plant Pat. No. 9,503), and the unpatented cultivar 'M. J. Cole'.

In general comparison to 'Flofetti', 'Fislamda' has a more intense flower color and more substantial (bigger) looking florets that consist of twice the number of petals. Furthermore, 'Fislamda' grows more vigorously, develops larger leaves, and appears more attractive at the beginning of flowering because of the many large buds that are already formed in this early stage.

In comparison to 'Fischic', 'Fislamda' has larger inflorescence and longer peduncles, foliage with distinct zonation, and more vigorous growth. In comparison to 'M. J. Cole', 'Fislamda' has bigger flowers with more petals and bigger buds with hair, while 'M. J. Cole' has narrow elliptic buds with smooth surfaces. Furthermore, 'Fislamda' grows more vigorously than 'M. J. Cole'.

BRIEF DESCRIPTION OF THE DRAWING

The accompanying color photographic drawing shows typical flower and foliage characteristics of 'Fislamda' with colors being as true as possible will illustrations of this type.

DETAILED BOTANICAL DESCRIPTION

The measurements were taken in Langley, British Columbia, Canada on May 26, 1998,—10 weeks after planting of rooted cuttings into 15-cm pots. The plants had not been pinched. In the following description, color references are made to The Royal Horticultural Society Colour Chart (R.H.S.). The color values were determined indoors from flowers developed in a greenhouse in May 1998 in Hillscheid, Germany.

Classification:

*Botanical.*—A hybrid of the species *Pelargonium peltatum L'Hérit.*

*Commercial.*—Ivy geranium, cv. 'Fislamda'.

Inflorescence:

*Umbel.*—Shape: Semi-spherical. Average diameter: 97 mm. Average depth: 52 mm. Peduncle length: 205 mm. Peduncle color: Light to medium green, RHS 143 B. Peduncle texture: Relatively strong (diameter 4–5 mm), smooth, with weak pubescence. Pedicel length: 23 mm, usually without 'joint'. Pedicel color: Lower part: Green, RHS 143 A. Upper part: Mainly green, but often a red stripe, RHS 60 A, develops along the length of the pedicel at the side most exposed to the sun. Number of flowers per umbel: Approximately 8–12. Lastingness of the individual umbel: 8–12 flowers or buds in various stages of development; the individual umbel lasts approximately 14 days in greenhouse conditions in spring at a temperature of 18° C.

*Corolla.*—Average diameter: 53 mm. Form: Double. Shape: Large, nearly round. Number of petals: 24–28. Number of petaloids: 2–4. Color (general tonality from a distance of three meters): Intense purple pink. Color of upper petals: RHS 67 A. Markings of upper petals: Strong, though often covered by inner petals, 2–4 black or very dark purple veins, with or without lighter stripes between, and a small dark purple spot in the middle of the petal. Color of lower petals: RHS 67 B. Color of lower surface of petals: RHS 61 C–D. Color of sepals: Green, RHS 137 D–143 A, anthocyanin only at the very base of the largest sepal can result in color near RHS 180 A or lighter. Number of sepals: 5. Texture of sepals: Smooth, with relatively strong pubescence.

*Bud (just before petals unfold).*—Shape: Broad elliptical. Color (sepals): Medium green, RHS 143 A. Color (petals): Pink, RHS 57 C, and white, marbled. Length: 16 mm. Width: 12 mm.

*Reproductive organs.*—Androecium: 3–5 fertile anthers, white to light-pink filaments, yellow-orange pollen. Gynoecium: 5–6-lobed stigma, dark-purple, RHS 59 A–B, whitish to light-pink style. Fertility/seed set: Hardly any spontaneous seed set.

*Spring flowering response period.*—In Hillscheid, Germany, in 1998, plants had on average 1.1 flowers opened 15 weeks after planting of unrooted cuttings.

*Outdoor flower production.*—Medium to rich flowering.

*Blooming habit.*—Continuous flowering from about May to mid-September; after which flowering may be poor depending on general conditions and light intensity. There is no noticeable fragrance.

*Lastingness of the individual bloom.*—The floret does not drop its petals easily (no 'shattering') and is not very susceptible to getting burned/scorched by the sun; the flower lasts approximately 9 days in greenhouse conditions in spring at a temperature of 18° C.

*Durability.*—Good shatter resistance; relatively good rain resistance.

Plant:

*Foliage.*—Form: Ivy-shaped, with weak, rounded lobes, closed base, and a flat leaf blade with smooth, slightly glossy (waxy) surface. Margin: Entire. Size of leaf: 95 mm wide. Color of upper surface: Medium green, RHS 137 B–C. Color of lower surface: RHS 137 D. Color of zonation: Brown, approximately RHS 166 A. Tolerance of botrytis: Fair.

*General appearance and form.*—Plant habit: Medium to tall, fairly round, moderately compact and moderately trailing. Internode length: 40–50 mm. Branching pattern: 5.8 naturally-occurring branches. Length of branches: 75 cm from the base of the main stem (soil surface), to the tips of the branches (in late August, based on 32-week-old plants).

I claim:

1. A new and distinct cultivar of geranium plant named 'Fislamda', as described and illustrated.

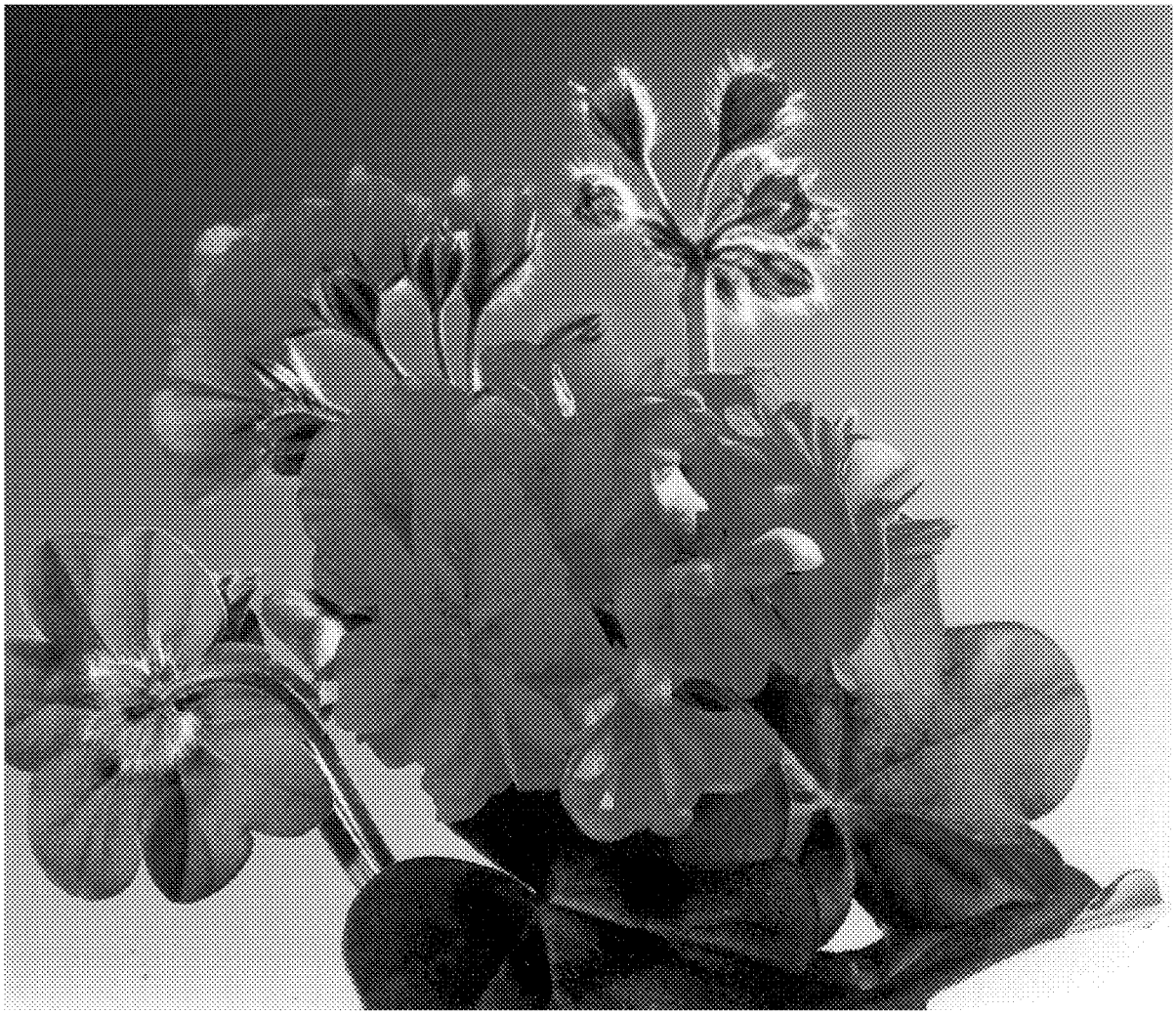

* * * * *